United States Patent [19] [11] 4,340,503
Rao et al. [45] Jul. 20, 1982

[54] CATALYST FOR CONVERTING SYNTHESIS GAS TO LIGHT OLEFINS

[75] Inventors: V. Udaya S. Rao, Monroeville; Robert J. Gormley, Pittsburgh, both of Pa.

[73] Assignee: The United States of America as represented by the United States Department of Energy, Washington, D.C.

[21] Appl. No.: 178,654

[22] Filed: Aug. 15, 1980

[51] Int. Cl.$^3$ .................. B01J 21/08; B01J 23/78
[52] U.S. Cl. ............................. 252/459; 518/719
[58] Field of Search ..................... 252/459; 518/719

[56] References Cited

U.S. PATENT DOCUMENTS

| | | | |
|---|---|---|---|
| 2,758,128 | 8/1956 | Rottig et al. | 260/449.6 |
| 2,819,283 | 1/1958 | Montgomery et al. | 518/719 X |
| 3,367,885 | 2/1968 | Rabo et al. | 252/455 Z |
| 4,010,008 | 3/1977 | Jo | 48/214 A |
| 4,061,724 | 12/1977 | Grose et al. | 423/335 |
| 4,073,750 | 2/1978 | Yates et al. | 252/459 |
| 4,154,751 | 5/1979 | McVickers et al. | 260/449.6 R |
| 4,159,995 | 7/1979 | Haag et al. | 518/719 X |
| 4,207,250 | 6/1980 | Butter et al. | 518/719 |

*Primary Examiner*—Carl F. Dees
*Attorney, Agent, or Firm*—Hugh W. Glenn; Robert J. Fisher; Richard G. Besha

[57] ABSTRACT

A catalyst and process for making same useful in the catalytic hydrogenation of carbon monoxide in which a silicalite support substantially free of aluminum is soaked in an aqueous solution of iron and potassium salts wherein the iron and potassium are present in concentrations such that the dried silicalite has iron present in the range of from about 5 to about 25 percent by weight and has potassium present in an amount not less than about 0.2 percent by weight, and thereafter the silicalite is dried and combined with amorphous silica as a binder for pellets, the catalytic pellets are used to convert synthesis gas to $C_2$–$C_4$ olefins.

11 Claims, No Drawings

CATALYST FOR CONVERTING SYNTHESIS GAS TO LIGHT OLEFINS

CONTRACTUAL ORIGIN OF THE INVENTION

The invention described herein was made in the course of, or under, a contract with the UNITED STATES DEPARTMENT OF ENERGY.

BACKGROUND OF THE INVENTION

Since the combined action in 1973 by OPEC which has resulted in a 500% increase in the cost of crude oil, the Fischer-Tropsch synthesis reaction has become more important. In countries with cheap coal, such as South Africa, Australia and even portions of the United States, the synthesis of fuel from coal can be economical today and will become more economical as OPEC continues to raise crude oil prices. In some countries as in the Federal Republic of Germany, the substitution of feedstock for the chemical industry rather than the production of fuel is the purpose behind increased research and development for the Fischer-Tropsch synthesis.

The chemical industry uses as feedstocks short chain olefins, particularly the $C_2$–$C_4$ olefins. It is well known that in the catalytic hydrogenation of carbon monoxide the type of catalyst used, the method of production and the synthesis conditions are critical in determining the yield types of hydrocarbons and oxygen-containing compounds produced. Thus by variations of the catalyst and the synthesis conditions a great flexibility in the production of hydrocarbons and oxygen-containing compounds of various boiling point ranges may be obtained.

Where substitutes for motor fuels are desired, Fischer-Tropsch synthesis catalysts have been developed which produce high yields of paraffin-like hydrocarbons having boiling points in the range of between approximately 30° and 180° C. including 5 to 10 carbon atoms in the molecule.

In order to produce the $C_2$–$C_4$ olefins without simultaneously producing large quantities of the corresponding paraffins, new catalysts must be developed which selectively produce the short chain olefins and simultaneously suppress or reduce the production of short chain paraffins.

For the conversion of synthesis gas to gasoline range hydrocarbons, various zeolite catalysts have been suggested. These catalysts have medium sized pores in the six angstrom range and in combination with iron have been shown to yield a high fraction of aromatics in the product, resulting in a favorable octane number around 90. It has been suggested that the transition metal component catalyzes the hydrogenation of carbon monoxide while the acid function of the zeolite support leads to an aromatic product. Due to the medium size pores there is a fairly sharp cut-off in the product distribution near the end of the gasoline range for the aromatic fraction. Since it has been shown that zeolites are selective to the production of gasoline range aromatic fractions, it is surprising to learn that a support structure without aluminum or having substantially no aluminum therein loaded with iron and a potassium promoter is not only selective to the $C_2$–$C_4$ olefins but also depresses or reduces the production of the corresponding $C_2$–$C_4$ paraffins.

Representative literature includes the Rabo et al U.S. Pat. No. 3,367,885 issued Feb. 6, 1968 describing a zeolite molecular sieve which undergoes a cation exchange process wherein about 40% of the aluminum ions are exchanged for non-metallic ions which are thereafter removed to decationize the sieve, thereby leaving a substantial amount of free aluminum ions. The sieves are then used as supports for catalytically active metals to prepare catalysts useful for hydrocarbon cracking.

The McVicker et al U.S. Pat. No. 4,154,751 issued May 15, 1979 discloses a catalyst useful in a Fischer-Tropsch synthesis reaction which a group VIII metal and promoter are deposited on a high surface area support. Potassium promoted iron is disclosed on an aluminum oxide support and various catalysts are tested to show the effects thereof on the products from the synthesis gas.

The Rottig et al U.S. Pat. No. 2,758,128 issued Aug. 7, 1956 relates to an unsupported iron catalyst which produces a high yield of gasoline-like hydrocarbons having from 5 to 10 carbon atoms in the molecule.

The Jo U.S. Pat. No. 4,010,008 issued Mar. 1, 1977 relates to a multiple-stage hydrocarbon steam reforming process for producing a methane-rich substitute natural gas.

Also of interest is the article in the Journal of Catalysis, Volume 15 (1969), pages 190 to 199 entitled Heats of Chemisorption on Promoted Iron Surfaces and the Role of Alkali in Fischer-Tropsch Synthesis by Dry et al. Also a paper entitled Catalytic Synthesis of Light Olefinic Hydrocarbons from CO and $H_2$ Over Some Iron Catalysts by C. H. Yang et al delivered at the Symposium on Advances in Fischer-Tropsch Chemistry presented before the Division of Petroleum Chemistry, Inc., American Chemical Society, Anaheim meeting, March 12–17, 1978 is interesting and pertains to the promotional effect of potassium, zinc, copper, magnesium, manganese and calcium on iron. Both supported and unsupported catalysts were tested. In the above paper no catalyst there reported showed a substantial olefin to paraffin ratio for the synthesis products.

SUMMARY OF THE INVENTION

It is a principal object of the invention to provide a catalyst useful in the hydrogenation of carbon monoxide which promotes the selective formation of $C_2$–$C_4$ olefins and suppresses formation of $C_2$–$C_4$ paraffins.

Another object of the invention is to provide a catalyst comprising a silicalite support having iron and potassium disbursed therethrough wherein the iron is present in a range of from about 5 to about 25% by weight of the silicalite and the potassium is present in an amount not less than about 0.2% by weight of the silicalite.

A further object of the invention is to provide in the process for the catalytic hydrogenation of carbon monoxide the improvement which comprises contacting synthesis gas with a catalyst of a silicalite support having iron and potassium disbursed therethrough, the iron being present in the range of from about 5 to about 25% by weight of the silicalite and the potassium being present in an amount not less than about 0.2% by weight of the silicalite, thereby resulting in the selective formation of $C_2$–$C_4$ olefins and suppressed formation of $C_2$–$C_4$ paraffins.

Yet another object of the invention is to provide a process for forming a catalyst useful in the catalytic hydrogenation of carbon monoxide comprising preparing a silicalite support substantially free of aluminum, soaking the silicalite support in an aqueous solution of iron and potassium salts wherein the iron and potassium are present in concentrations such that the dried silicalite has iron present in the range of from about 5 to about 25% by weight and has potassium present in an amount not less than 0.2% by weight, and drying the silicalite.

These and other objects of the present invention may more readily be understood by reference to the following specification.

DETAILED DESCRIPTION OF THE INVENTION

The starting material for the preparation of the invention catalyst is a molecular sieve form of crystalline silica identified hereinafter as silicalite described in U.S. Pat. No. 4,061,724 issued to Grose et al Dec. 6, 1977 for Crystalline Silica, the disclosure thereof being incorporated herein by reference. Any of the methods described in the aforementioned patent may be used for the preparation of the starting material of the inventive catalysts. It is believed that the significant difference between the zeolites previously used in catalysts as supports for iron having a potassium promoter is that silicalite is substantially pure silicon dioxide with only trace amounts of aluminum or alumina as an unwanted impurity, alumina or aluminum being present in silicalite in an amount not greater than about 1000 parts per million.

In order to prepare the inventive catalyst, the starting material is prepared according to one of the methods set forth in the above-captioned patent and is impregnated with iron and potassium as follows: A solution of potassium nitrate and ferric nitrate (with 9 molecules of water of hydration), is made with the proportion of the potassium nitrate and ferric nitrate in the ratio of 1 to 19.8 by weight. The aqueous solution is added to a previously calcined and dried silicalite until incipient wetness is reached. The relative amounts of silicalite and the above nitrate solution are such as to yield a catalyst containing 7.8% by weight iron and 0.9% by weight potassium after drying and subsequent reduction. The impregnation of silicalite with the iron and potassium nitrates is carried out for one hour under a slight vacuum to enable the solution to enter the pores, the slight vacuum resulting in the degasing of the silicalite. The catalyst is dried with constant stirring over a boiling water bath and then is dried overnight at 110° C.

This material is then formed into pellets in order to yield a good crush strength for the catalyst. In order to prepare pellets of the silicalite material, a binder is necessary such as amorphous silica obtainable as Ludox AS-40, the amorphous silica being mixed with the impregnated silicalite at a weight ratio of about 1:10 by weight. The mixture is thereafter stirred and formed into pellets to yield tablets ⅛ inch in diameter which are dried at 110° C. overnight to yield the subject catalyst. The catalyst thus prepared is a silicalite (7.8% Fe, 0.9% K). The amorphous silica component is merely used as a binder and does not provide any important catalytic function.

The silicalite useful in the present invention should not contain more than about 1000 parts per million aluminum as it is believed that aluminum in excess of this amount provides too much acidity to the silicalite resulting in an increased production of the paraffins with a corresponding decrease in the olefin to paraffin ratio.

Iron may be present in the range of from about 5% by weight of the silicalite to about 25% by weight of the silicalite, with the preferred catalyst having iron present in the range of from about 6% by weight of the silicalite to about 10% by weight of the silicalite. If less than about 5% by weight of iron is used the conversion fraction decreases, that is the rate of conversion is too low and the catalyst is impracticable from a commercial view point. If more than about 25 weight percent iron is used the selectivity of the catalyst to olefins decreases because the particle size of the iron is too large resulting in a lower dispersion of the iron through the silicalite and the silicalite becomes blocked.

Potassium must be present in an amount not less than about 0.2% by weight of the silicalite in order to be an effective promoter for the iron. If less than about 0.2% by weight of potassium is present then the iron is not sufficiently promoted and the conversion rate is too low to be practicable. If more than about 3% by weight potassium is added, then the potassium becomes a diluent to the catalyst and may block availability to the silicalite pores. Where potassium is present in the range of from about 0.2% by weight to about 3% by weight the potassium acts as a promoter for the iron, the preferred range for the inventive catalyst being 0.5% by weight to about 2% by weight of the silicalite.

The catalyst of the subject invention produces a higher olefin to paraffin ratio in the product which is important because the resulting separation of paraffins from the $C_2$–$C_4$ olefins is less expensive, thereby enhancing the economics of the subject process. By providing a catalyst in the Fischer-Tropsch synthesis reaction which is selective to the $C_2$–$C_4$ olefin while at the same time suppressing the production of the $C_2$–$C_4$ paraffins, feedstocks for the chemical industry can be obtained more economically resulting in decreased dependence on foreign petroleum products.

Although in the example described, the silicalite was loaded with the nitrate salts of both iron and potassium, any water soluble salt including acetates, sulfates or the like may be used in the process of preparing the inventive catalysts. Some salts such as the halides result in a catalyst which is more acidic adversely affecting the desired olefin to paraffin ratio, and these salts are to be avoided. Although the ferric ion was used in the preparation of the inventive catalyst, ferrous ion may also initially be used, but the ferrous ions tend to be converted to the ferric ion during the process, whereby no significance is attached to whether the water soluble salt is ferrous, ferric or another form of iron. Alternatively, the catalyst can be made by admixing the silicalite powder physically with a powder of precipitated iron catalyst promoted with potassium and compacting the mixture to yield tablets of the requisite size.

The catalytic pellets are reduced by contact with hydrogen gas in the temperature range of between about 300° C. and about 500° C. to provide about 85 to 86% conversion of the nitrate to the free metal. Since the silicalite support contains some oxygen, 100% conversion of the nitrates to the free metal is generally not obtained. The preferred temperature range for the reduction is between about 400° C. and about 450° C. with higher temperatures being unnecessary and lower temperatures providing a reaction rate which is too slow to be economically desirable. Generally, the hydrogen gas is provided at one atmosphere.

The reduced catalyst is contacted with a carbon containing gas, preferably carbon monoxide in order to provide iron carbide ($Fe_2C$) and potassium which is not carbided, this reaction preferably being at a very controlled temperature in the range of from 200° C. to about 250° C. in order to control the temperature of the exothermic reaction. The carbiding of the free iron contained in the reduced catalyst may take place in a fluidized bed reactor which is also used for the catalytic hydrogenation of carbon monoxide. In fact, the synthesis gas of carbon monoxide and hydrogen may be used for the carbiding step. However, the carbiding reaction is usually at a lower temperature, that is the aforesaid 200° C. to about 250° C., than is the subsequent catalytic hydrogenation of carbon monoxide which may be carried out at about 280° C. In practice, the silicalite containing the free metal is very slowly carbided over a period of a few days in order to obtain the required carbide-form which is the high Curie point form of the Hagg carbide.

The catalyst has been tested in both a fixed bed microreactor and a Berty continuous-flow stirred tank reactor. The microreactor generally is used for testing small catalyst samples having a volume of about 1 milliter while the Berty reactor can be used for larger samples having a volume of about 60 milliters. High conversion rates of synthesis gas to olefins were obtained using the subject catalysts in tests conducted in both the micro-reactor and the Berty reactor. Comparisons are hereinafter set forth in the following table with catalyst described by Kolbel et al reported in the November 1978 edition of the Society of Automotive Engineers, Inc. which was a reprint of the paper entitled Feedstock For Chemical Industry by Selective Fischer-Tropsch Synthese by Kolbel et al delivered at the 13th Intersociety Energy Conversion Engineering Conference. In that paper, a manganese promoted iron catalyst was used with a synthesis gas to provide a high selectivity to the $C_2$-$C_4$ olefins, however the $C_2$-$C_4$ paraffins were also produced in relatively substantial amounts, thereby resulting in an olefin to paraffin ratio of about 4.

As will be shown in the Table, the subject catalysts routinely provide olefin to paraffin ratios greater than 10 and with values greater than 45 being obtained. Accordingly, the inventive catalysts represents a major improvement over catalysts reported in the literature.

previously reported for the silicalite (7.8% Fe, 0.9% K) catalyst produced 12.0 weight percent $C_2H_4$, 2.5 weight percent $C_2H_6$, 17.3 weight percent $C_3H_6$, and less than 0.2 weight percent $C_3H_8$, $C_4H_{10}$ and $C_4H_8$. The $C_2$-$C_4$ olefin to $C_2$-$C_4$ paraffin ratio was about 11.7 and the olefin production was about 29.3 percent. From the foregoing examples, it is clear that the inventive catalysts are entirely effective to produce $C_2$-$C_4$ olefin to $C_2$-$C_4$ paraffin ratios in excess of 10, while maintaining the $C_2$-$C_4$ olefin production rate at least about 30 percent by weight of the products.

The catalyst other than the silicalite supported iron-potassium catalysts which are the zeolite supported catalyst or the precipitated iron-manganese catalyst of Kolbel et al or the unpromoted silicalite —Fe catalyst do not produce the same olefin to paraffin ratios but in fact have ratios substantially less than 10. The catalyst described by Kolbel et al was the best in that the olefin to paraffin ratio was 4 whereas the zeolite catalyst had an olefin to paraffin ratio of 0.44 and the unpromoted silicalite —Fe catalyst had a ratio of 0.87. Accordingly, it is seen that the inventive catalyst is vastly superior to the available catalysts tested in diminishing or suppressing the production of the $C_2$-$C_4$ paraffins while retaining a high production of the $C_2$-$C_4$ olefins.

While there has been disclosed what at present is considered to be the preferred embodiment of the present invention, it will be understood that various modifications and alterations may be made therein without departing from the true scope of the present invention, and it is intended to cover herein all such variations and modifications therein.

The embodiments of the invention in which an exclusive property or privilege is claimed are defined as follows:

1. A catalyst comprising a silicalite support having iron and potassium dispersed therethrough wherein said iron is present in the range of from about 5 to about 25 percent by weight of the silicalite and the potassium is present in an amount not less than about 0.2 percent by weight of the silicalite, said silicalite support is substantially aluminum free having less than about 1000 parts per million aluminum.

2. The catalyst of claim 1 wherein the silicalite has a

TABLE

| Catalyst | ZSM-5 (14.1% Fe) | Silicalite (13.6% Fe) | Silicalite (7.8% Fe, 0.9% K) | Precip. Fe—Mn (Kolbel et al) |
|---|---|---|---|---|
| Press. (Bar) | 21 | 21 | 21 | 14 |
| Temp. (°C.) | 280 | 280 | 280 | 290 |
| $H_2$/CO Ratio | 1.3 | 1.0 | 0.9 | 0.8 |
| Sp. Vel. ($h^{-1}$) | 1000 | 1000 | 1300 | 353 |
| Prod. Comp. % | | | | |
| $CH_4$ | 25.5 | 18.6 | 8.6 | 12.1 |
| $C_2H_4$ | 1.9 | 3.8 | 8.2 | 7.6 |
| $C_2H_6$ | 11.8 | 11.5 | 0.4 | 4.9 |
| $C_3H_6$ | 3.4 | 11.1 | 19.3 | 17.3 |
| $C_3H_8$ | 5.5 | 5.5 | 0.2 | 2.1 |
| $C_4H_8$ | 3.6 | 0.0 | 8.6 | 15.2 |
| $C_4H_{10}$ | 2.7 | 0.0 | 0.2 | 3.1 |
| $C_2$-$C_4$ Olefins | 8.9 | 14.9 | 36.1 | 40.1 |
| $C_2$-$C_4$ Paraffins | 20.0 | 17.0 | 0.8 | 10.1 |
| $C_5+$ and oxygenates | 45.6 | 41.8 | 55.1 | 47.8 |
| $\dfrac{C_2\text{-}C_4 \text{ Olefins}}{C_2\text{-}C_4 \text{ Paraffins}}$ | 0.44 | 0.87 | 45.1 | 4.0 |

An additional silicalite based catalyst was produced according to the process disclosed herein, wherein the final catalyst had 22.3% by weight iron and 2.3% by weight potassium promoter. A test of the catalyst with the synthesis gas using substantially the same conditions pore size of about 6 Angstroms.

3. The catalyst of claim 1 wherein the iron is present as iron carbide.

4. The catalyst of claim 1 wherein the iron is present as the high Curie point form of the Hagg carbide.

5. The catalyst of claim 1 wherein the iron is present in the range of from about 6 percent to about 10 percent by weight of the silicalite.

6. The catalyst of claim 1 wherein the potassium is present in the range of from about 0.5 percent to about 2 percent by weight of the silicalite.

7. The catalyst of claim 1 wherein the silicalite is in the form of pellets having up to about 10 percent by weight of amorphous silica present as a binder.

8. A process for forming a catalyst useful in the catalytic hydrogenation of carbon monoxide comprising preparing a silicalite support substantially free of aluminum, soaking the silicalite support in an aqueous solution of water-soluble iron salts and potassium salts wherein the iron and potassium are present in concentrations such that the dried silicalite has iron present in the range of from about 5 to about 25 percent by weight and has potassium present in an amount not less than about 0.2 percent by weight, and drying the silicalite.

9. The process of claim 8 wherein the water-soluble salts of potassium and iron are nitrates.

10. The process of claim 8 wherein the soaked silicalite is first dried over a boiling water bath and then dried under vacuum to remove gas from the silicalite pores.

11. The process of claim 8 and further comprising mixing the dried silicalite with up to about 10 percent by weight amorphous silica as a binder and thereafter forming the mixture into pellets.

* * * * *